United States Patent [19]

Watanabe et al.

[11] Patent Number: 5,084,584

[45] Date of Patent: Jan. 28, 1992

[54] PROCESS FOR PRODUCING AN α-ACYLOXY-α,β-UNSATURATED CARBONYL COMPOUND AND A 20-ACYLOXY-17(20)-METHYLEN-21-AL-STEROID COMPOUND

[75] Inventors: Kiyoshi Watanabe, Yokohama; Hideaki Kataoka, Kamakura; Kuniaki Goto, Tokyo, all of Japan

[73] Assignee: Nippon Zeon Co., Ltd., Tokyo, Japan

[21] Appl. No.: 593,586

[22] Filed: Oct. 9, 1990

Related U.S. Application Data

[63] Continuation of Ser. No. 242,109, Sep. 9, 1988, abandoned.

[30] Foreign Application Priority Data

Sep. 11, 1987 [JP] Japan ................ 62-228054
Sep. 11, 1987 [JP] Japan ................ 62-228055
Sep. 11, 1987 [JP] Japan ................ 62-228056

[51] Int. Cl.⁵ ............... C07J 13/00; C07C 69/76; C07C 69/52; C07C 69/02
[52] U.S. Cl. .................. 552/530; 552/532; 560/8; 560/106; 560/205; 560/220; 560/225; 560/231
[58] Field of Search ............ 560/19, 51, 55, 66, 560/67, 75, 113, 155, 174, 179, 219, 226, 229, 262, 8, 106, 205, 220, 225, 231; 552/530, 532

[56] References Cited

U.S. PATENT DOCUMENTS

| | | | |
|---|---|---|---|
| 3,255,218 | 6/1966 | Herzog | 552/532 |
| 3,842,105 | 10/1974 | Hofmeister et al. | 260/397.45 |
| 4,216,159 | 8/1980 | Hessler et al. | 260/397.1 |
| 4,530,795 | 7/1985 | Huber | 552/595 |

FOREIGN PATENT DOCUMENTS

2920290 12/1979 Fed. Rep. of Germany.

OTHER PUBLICATIONS

Mattox, JACS, "Steroids Derived from Bile Acids. XV. The Formation of a Glyoxal Side Chain at C-17 from Steroids with Dihydroxyacetone and Δ¹⁶-Ketol Side Chains", vol. 74, pp. 4340–4347 (1987).
Methoden der Organischen Chemie (Houben Weyl), 4th Ed., vol. V/2A, 1977, Jager et al., "Oxidation von Alkinen", pp. 677–686.
CA; vol. 111 (1989) #23793k; Watanabe et al.
CA; vol. 86 (1977) #16876b; Robins et al.
CA; vol. 92 (1980) #215688r; Robins et al.
CA; vol. 96 (1982) #69459f; Chiang.
CA; vol. 107 (1987) #77485x; Ireland et al.

Primary Examiner—Frederick E. Waddell
Assistant Examiner—Kimberly R. Jordan
Attorney, Agent, or Firm—Armstrong, Nikaido, Marmelstein, Kubovcik & Murray

[57] ABSTRACT

There are disclosed a process for producing an α-acyloxy-α,β-unsaturated carbonyl compound represented by the general formula (VI):

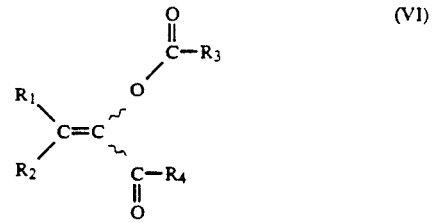

wherein $R_1$, $R_2$ and $R_4$ are independently hydrogen atoms or substituted or unsubstituted hydrocarbon residues, or $R_1$ and $R_2$, when taken together with one another in an optional combination, form a ring, $R_3$ is a substituted or unsubstituted hydrocarbon residue, and 〰 indicates that the configuration may be either E-configuration or Z-configuration, in particular, a 20-acyloxy-17(20)-methylen-21-al-steroid represented by the partial structural formula (II):

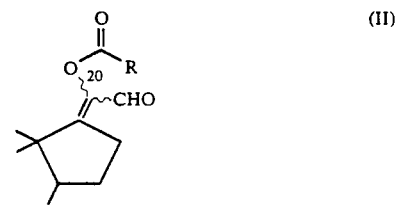

wherein R is a hydrocarbon residue, and 〰 indicates that the configuration of the acyloxy group and the formyl group bonded to the carbon atom at the 20-position may be either E-configuration or Z-configuration, which comprises oxidizing a propargyl ester represented by the general formula (V):

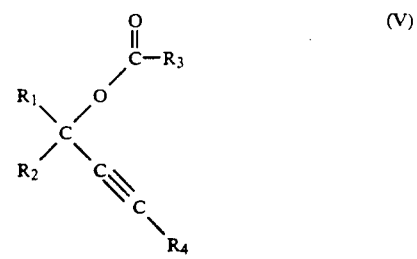

wherein $R_1$, $R_2$, $R_3$ and $R_4$ have the same meanings as defined above; an al-steroid compound having the above partial structural formula which is an intermediate for producing a 21-acyloxy-20-keto-delta¹⁶-steroid being extremely useful as an intermediate for important corticoids as drugs and obtained by being subjected said al-steroid to isomerization reaction; and a process for producing a 21-acyloxy-20-keto-delta¹⁶-steroid which comprises oxidation reaction and isomerization reaction.

6 Claims, No Drawings

PROCESS FOR PRODUCING AN α-ACYLOXY-α,β-UNSATURATED CARBONYL COMPOUND AND A 20-ACYLOXY-17(20)-METHYLEN-21-AL-STEROID COMPOUND

This application is a continuation of application Ser. No. 242,109 filed Sept. 9, 1988 now abandoned.

FIELD OF THE INVENTION

This invention relates to a novel process for producing a 21-acyloxy-20-keto-delta[16]-steroid and more particularly it relates to a process for producing a 21-acyloxy-20-keto-delta[16]-steroid via a 20-acyloxy17(20)-methylen-21-al-steroid by using a 17-α-ethynyl17-β-acyloxysteroid.

This invention also relates to a 20-acyloxy17(20)-methylen-21-al-steroid which is novel as a steroid intermediate useful for a 21-acyloxy-20-keto-delta[16]-steroid.

DISCUSSION ON RELATED ART

21-Acyloxy-20-keto-delta[16]-steroids (the partial structural formula (III) hereinafter shown) have heretofore been known as key intermediates for producing corticoids which are important as drugs (U.S. Pat. No. 4530795, Jap. Pat. Pub. No. 33-2128, and Jap. Pat. Appln. Kokai (Laid-Open) No. 61-72798).

Synthesis of such 21-acyloxy-20-keto-delta[16]steroids are earnesty investigated. For example, there are known processes for producing a 16-unsaturated steroid using a 21-acyloxy-20-keto-17-α-hydroxysteroid as a starting material (U.S. Pat. Nos. 3839369, 3493563 and 3631076, etc.). These processes, however, use expensive corticoid itself as a starting material or an intermediate and hence are not suitable for producing a 21-acyloxy-20-keto-delta16-steroid industrially at low cost.

On the other hand, 17-ketosteroids (see the partial structural formula (III') shown below) such as androsta-4-ene-3,20-dione and 9α-hydroxy-androsta-4-ene3,20-dione have recently come to be produced at low cost from sterols such as cholesterol or sitosterol by a fermentation method:

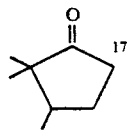

Therefore, there have been made a large number of studies of processes for producing corticoids from these 17-ketosteroids (Jap. Pat. Appln. Kokai (Laid-Open) Nos. 52-62265 and 56-22800, etc.). However, there have been reported few processes for producing 21-acyloxy-20-keto-delta[16]-steroids from 17-ketosteroids (See Jap. Pat. Appln. Kokai (Laid-Open) No. 59-206400), and development of a more effective process has been desired.

SUMMARY OF THE INVENTION

Accordingly, in order to develop a novel process for producing corticoids using these 17-ketosteroids, the present inventors earnestly investigated, and consequently found that when a 17α-ethynyl-17β-acyloxysteroid (the partial structural formula (I) shown below) which can be easily obtained from a 17-ketosteroid by a conventional method is used as a starting material and oxidized into a 20-acyloxy-17(20)-methylen-21-alsteroid (the partial structural formula (II) shown below), which is then isomerized, a desired 21-acyloxy-20-ketodelta[16]-steroid (the partial structural formula (III) shown below) can be obtained by a short process economically in high yield. On the basis of the above finding, the present invention has been accomplished.

The 1st aspect of the invention is directed to a process for producing a 21-acyloxy-20-keto-delta[16]-steroid having the partial structural formula (III) which comprises oxidizing a steroid having the partial structural formula (I) into a steroid having the partial structural formula (II), and then isomerizing this steroid:

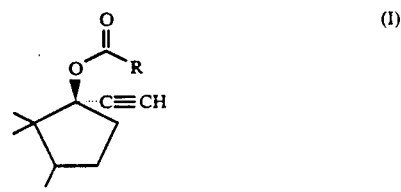

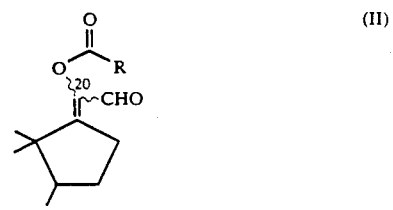

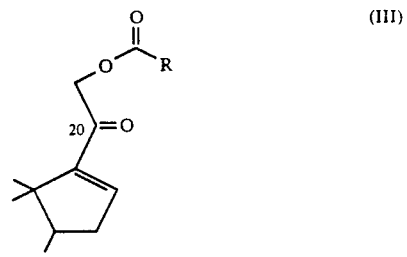

wherein R is a hydrocarbon residue, and $\sim$ indicates that the configuration of the acyloxy group and the formyl group bonded to the carbon atom at the 20-position may be either E-configuration or Z-configuration.

The 2nd aspect of the present invention is directed to a process for producing an α-acyloxy-α,β-unsaturated carbonyl compound represented by the general formula (VI):

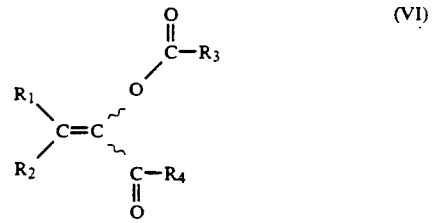

wherein $R_1$, $R_2$ and $R_4$ are independently hydrogen atoms or substituted or unsubstituted hydrocarbon residues, or $R_1$, $R_2$ and $R_4$, when taken together with one another in an optional combination, form a ring, $R_3$ is a substituted or unsubstituted hydrocarbon residue, and $\sim$ indicates that the configuration may be either E-configuration or Z-configuration, which comprises bringing a propargyl ester represented by the general formula (V):

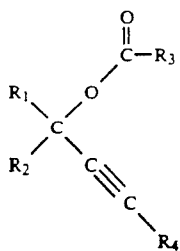

(V)

wherein $R_1$, $R_2$, $R_3$ and $R_4$ have the same meanings as defined above, into contact with a platinum group metal compound catalyst in the presence of oxygen and/or a peroxide. The 3rd aspect of the invention is directed to a 20-acyloxy-17(20)-methylen-21-al-steroid of the following general formula (IV) which is an intermediate for producing the above-mentioned 21-acyloxy-20-ketodelta[16]-steroid (III):

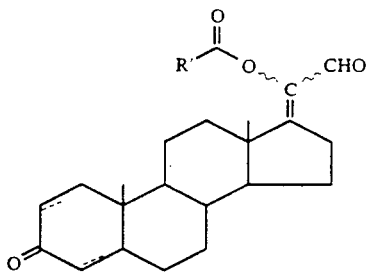

(IV)

wherein R' is a lower alkyl group, ∼∼∼ indicates the same as in the above partial structural formula, and ═ is a single bond or a double bond.

DETAILED DESCRIPTION OF PREFERRED EMBODIMENTS

The steroid used as starting material in the 1st aspect of the invention is a 17-α-ethynyl-17-β-acyloxysteroid having the above partial structural formula (I), which can be obtained by ethynylating a 17-ketosteroid at the 17-position into a 17-α-ethynyl17β-hydroxysteroid by a conventional method, and then acylating the 17-β-hydroxyl group (Jap. Pat. Pub. No. 53-8695, Journal of Organic Chemistry, 44, 1582-1584 (1979), etc.).

In the above partial structural formula (I), R constituting the acyloxy group portion is not critical so long as it is a hydrocarbon residue. Specific examples of R include alkyl groups such as methyl, ethyl, propyl, isopropyl, butyl, isobutyl, hexyl, octyl, decyl, and the like; alkenyl groups such as allyl, pulenyl, and the like; and aryl groups such as phenyl, benzyl, and the like. Among them, alkyl groups having 5 or less carbon atoms are preferred.

The 17-α-ethynyl-17-β-acyloxysteroid having the partial structural formula (I) explained above is, for example, a steroid compound represented by the structural formula:

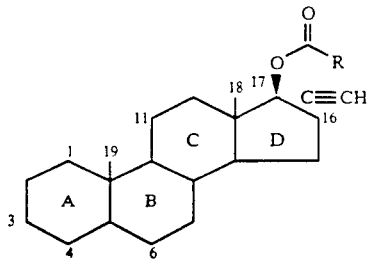

In the present invention, the steroid skeleton portion may be either a steroid whose ring A has an aromatic nucleus, such as mestranol, or a 19-norsteroid such as 19-norethisterone. In the case of a steroid having a carbonyl group at the 3-position, the carbonyl group may be protected in the form of an acetal, enol or enamine. Furthermore, the steroid compound is optionally substituted by substituents, for example, hydroxyl groups at the 1-, 6- and 11-positions, a keto group at the 11-position, fluorine atoms at the 6- and 9-positions, and methyl groups at the 1-, 6- and 16-positions.

Specific examples of the 17-α-ethynyl-17-β-acyloxysteroid include 17-α-ethynyl-17β-acyloxy-androsta4-en-3-one, 17α-ethynyl-17β-acyloxy-androsta-1,4-dien3-one, 17α-ethynyl-17β-acyloxy-androsta-4,9(11)-dien3-one, 17α-ethynyl-17β-acyloxy-androsta-1,4,9(11)-trien3-one, 17α-ethynyl-17β-acyloxy-3β-acetoxy-androsta-5-ene, etc.

In the 1st aspect of the invention, a starting material having the above partial structural formula (I) is first oxidized to obtain a steroid having the partial structural formula (II). The oxidation reaction is carried out, for example by bringing the starting material into contact with a platinum group metal compound catalyst in the presence of oxygen and/or a peroxide.

Although not critical, the partial pressure of oxygen in the reaction system is usually 0.1 to 1 atmospheric pressure. If necessary, the reaction can be carried out in an atmosphere of a mixed gas with an inert gas such as nitrogen.

The peroxide used includes, for example, peroxy acids such as peracetic acid, performic acid, perbenzoic acid, methachloroperbenzoic acid, monoperphthalic acid, trifluoroperacetic acid, and the like; alkyl hydroperoxides such as t-butylhydroperoxide, hydrogen peroxide, aqueous hydrogen peroxide, peroxosulfuric acid, cumene hydroperoxide, and the like; dialkyl peroxides such as di-t-butyl peroxide, dicumyl peroxide, and the like; diacyl peroxides such as benzoyl peroxide, di-p-chlorobenzoyl peroxide, diisopropyl perdicarbonate, and the like; peroxy acid esters such as t-butyl perbenzoate, di-t-butyl peracetate, and the like; and halogenous acids such as sodium hypochlorite, sodium hypobromite, sodium iodite, potassium hypochlorite, sodium chlorite, sodium bromite, sodium iodite, potassium chlorite, sodium chlorate, sodium bromate, perchloric acid, sodium perchlorate, periodic acid, sodium periodate, and the like.

Although the using amount of the peroxide is properly selected, the peroxide is used usually in an amount of 1 to 10 moles, preferably 1 to 5 moles per mole of the starting material.

The platinum group metal compound catalyst is a salt or complex of palladium, ruthenium, platinum, rhodium or the like. Specific examples of the catalyst include palladium chloride, palladium bromide, palladium iodide, dichlorobis(acetonitrile)palladium, dibromobis(acetonitrile)palladium, dichlorobis(benzonitrile)palladium, dibromobis(benzonitrile)palladium, sodium palladium (II) chloride, potassium palladium (II) chloride, sodium palladium (II) bromide, potassium palladium (II) bromide, lithium palladium (II) bromide, palladium nitrate, palladium sulfate, palladium acetate, potassium hexachloroplatinate, rhodium chloride, ruthenium chloride, etc. Among platinum metals, palladium is preferred from the viewpoint of reactivity, and divalent palladium halides are particularly preferred.

Although the using amount of the platinum group metal compound catalyst is properly selected, the catalyst is used usually in an amount of 0.01 to 10 moles, preferably 0.1 to 5 moles per 100 moles of the starting material.

A copper compound may be present in the reaction system as a co-catalyst. Specific examples of the copper compound include cupric chloride, cupric bromide, cupric acetate, cupric iodide, cupric formate, etc.

These co-catalysts are used usually in an amount of 0.1 to 50 moles, preferably 0.1 to 5 moles per 100 moles of the starting material. Their employment permits improvement of the activity of reaction.

In the present invention, for improvement of the reactivity and the yield, etc., it is preferable to carry out the oxidation reaction in the presence of an acid. Specific examples of the acid include organic acids such as formic acid, acetic acid, propionic acid, p-toluenesulfonic acid, and the like, and inorganic acids such as hydrochloric acid, hydrobromic acid, hydroiodic acid, and the like. Among them, formic acid and hydrobromic acid are preferred from the viewpoint of the reactivity and the like.

Although the using amount of the acid is properly selected, it is usually 0.01 to 10 moles, preferably 0.01 to 5 moles per mole of the starting material, and the most suitable amount varies depending on the acid used.

A diluent may be present in the reaction system. Specific examples of the diluent include water; nitriles such as acetonitrile, propionitrile, benzonitrile, and the like; amides such as dimethylformamide, diethylformamide, dimethylacetamide, N-methylpyrrolidone, and the like; ethers such as tetrahydrofuran, dioxane, dibutyl ether, ethylene glycol dimethyl ether, and the like; ketones such as acetone, methyl ethyl ketone, methyl isobutyl ketone, cyclohexanone, and the like; esters such as ethyl acetate, propyl acetate, methyl propionate, and the like; alcohols such as methanol, ethanol, propanol, tert-butanol, diethylene glycol monoethyl ether, and the like; sulfoxides such as dimethyl sulfoxide, diethyl sulfoxide, and the like; organic solvents such as benzene, toluene, xylene, and the like; and mixed solvents thereof with water. Among them, the nitriles, the amides and the ethers are preferred.

These diluents are used usually in such an amount that the concentration of the starting material becomes 1 to 50% by weight. Their employment permits improvement of the activity of reaction and the stability of catalyst.

The reaction temperature is usually 0° C. or higher, preferably 20° C. to 100° C. The reaction time is usually 5 minutes to 30 hours.

After completion of the reaction, if necessary, the reaction product is separated from the reaction solution by a conventional method such as solvent extraction, distillation, recrystallization, column chromatography, etc., whereby a 20-acyloxy-17(20)-methylen-21-al-steroid having the partial structural formula (II) can be obtained with a high purity. It is also possible to subject the reaction product to the subsequent step without purification.

The 20-acyloxy-17(20)-methylen-21-al-steroid thus obtained is a mixture of two forms in which the configuration of the acyloxy group and the formyl group bonded to the carbon atom at the 20-position is E-configuration or Z-configuration, and it is, for example, a steroid compound represented by the structural formula:

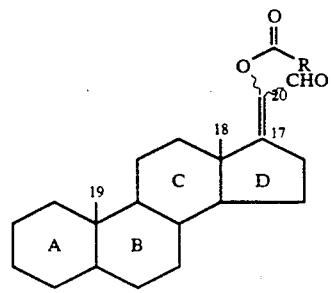

The acyloxy group at the 20-position is a group which has migrated from the 17$\beta$ position of the 17$\alpha$-ethynyl17$\beta$-acyloxysteroid, i.e., the starting material. For example, from a 17$\alpha$-ethynyl-17$\beta$-acetoxysteroid, a 20-acetoxy-17(20)-methylen-21-al-steroid can be obtained, and from a 17$\alpha$-ethynyl-17$\beta$-isobutyryloxysteroid, a 20-isobutyryloxy-17(20)-methylen-21-al-steroid can be obtained.

The substituents and structures in the portions other than the 17-, 20- and 21-positions are not changed by the reaction, and steroids retaining the respective partial structures can be obtained.

Among such steroids having the partial structural formula (II), 20-acyloxy-17(20)-methylen-21-al-steroids of the above general formula (IV) are novel substances which have not been known in any literature and are useful as intermediates for synthesizing 21-acyloxy-20-keto-delta[16]-steroids which are key compounds for synthesizing corticoids.

In the above general formula (IV), R' is a lower alkyl group. Specific examples of the lower alkyl group include methyl group, ethyl group, propyl group, isopropyl group, butyl group, isobutyl group, pentyl group, etc.

Specific examples of the 20-acyloxy-17(20)-methylen-21-al-steroid include 20-acetoxy-3-oxo-pregna4,17(20)-dien-21-al, 20-propionyloxy-3-oxo-pregna4,17(20)-dien-21-al, 20-butyryloxy-3-oxo-pregna4,17(20)-dien-21-al, 20-isobutyryloxy-3-oxo-pregna4,17(20)-dien-21-al, 20-valeryloxy-3-oxo-pregna4,17(20)-dien-21-al, 20-isovaleryloxy-3-oxo-pregna4,17(20)-dien-21-al, 20-caproyloxy-3-oxo-pregna4,17(20)-dien-21-al, 20-isocaproyloxy-3-oxo-pregna4,17(20)-dien-21-al, 20-acetoxy-3-oxo-pregna-4,9(11), 17(20)-trien-21-al, 20-propionyloxy-3-oxo-pregna4,9(11), 17(20)-trien-21-al, 20-butyryloxy-3-oxopregna-4,9(11), 17(20)-trien-21-al, 20-isobutyryloxy3-oxo-pregna-4,9(11), 17(20)-trien-21-al, 20-valeryloxy-3-oxo-pregna-4,9(11), 17(20)-trien-21-al, 20-isovaleryloxy-3-oxo-pregna-4,9(11),17(20)-trien-21-al, 20-caproyloxy-3-oxo-pregna-4,9(11),17(20)-trien-21-al, 20-isocaproyloxy -3-oxo-pregna-4,9(11),17(20)-trien-21-al, 20-acetoxy-3-oxo-pregna-1,4,17(20)-trien- 21-al, 20-propionyloxy-3-oxo-pregna-1,4,17(20)-trien-21-al, 20-butyryloxy-3-oxo-pregna-1,4,17(20)-trien-21-al, 20-isobutyryloxy-3-oxo-pregna-1,4,17(20)-trien-21-al, 20-valeryloxy-3-oxo-pregna-1,4,17(20)-trien-21-al, 20-isovaleryloxy-3-oxo-pregna-1,4,17(20)-trien-21-al, 20-caproyloxy-3-oxo-pregna-1,4,17(20)-trien-21-al, 20-isocaproyloxy-3-oxo-pregna-1,4,17(20)-trien-21-al, 20-acetoxy-3-oxo-pregna-1,4,9(11),17(20)-tetraen-21-al, 20-propionyl-3-oxo-pregna-1,4,9(11),17(20)-tetraen-21-al, 20-butyryloxy-3-oxo-pregna-1,4,9(11),17(20)-tetraen-21-al, 20-isobutyryloxy-3-oxo-pregna-1,4,9(11),17(20)-tetraen21-al, 20-valeryloxy-3-oxo-pregna-1,4,9(11), 17(20)-tetraen-21-al, 20-isovaleryloxy-3-oxopregna-1,4,9(11), 17(20)-tetraen-21-al, 20-caproyloxy-3-oxo-pregna-1,4,9(11), 17(20)-tetraen-21-al, 20-isocaproyloxy-3-oxo-pregna-1,4,9(11),17(20)-tetraen21-al, etc.

In the present invention, the 20-acyloxy17(20)-methylen-21-al-steroid having the partial structural formula (II) is subsequently isomerized, whereby a 21-acyloxy-20-keto-delta[16]-steroid having the partial structural formula (III), i.e., a desired compound, can be obtained.

Although a method for the isomerization is not critical, the isomerization is carried out, for example, by treating said steroid having the partial structural formula (II) with a isomerization catalyst in an organic polar solvent.

The organic polar solvent includes, for example, pyridine, N-methylpyrrolidone, dimetyl sulfoxide, dimethylformamide, dimethylacetamide, acetonitrile, dimethoxyethane, tetrahydrofuran, methanol, ethanol, propanol, tert-butanol. ethyl acetate, propyl acetate and the like. Among them, dimethylformamide and ethyl acetate are preferred.

Specific examples of the isomerization catalyst include metal salts of carboxylic acids, carbonic acid (e g., U.S. Pat. No. 3842105) and non-nucleophilic strong bases. Specific examples of carboxylic acids constituting the carboxylic acid metal salts include lower aliphatic carboxylic acids having 5 or less carbon atoms, such as acetic acid, propionic acid, butyric acid, etc.; and aromatic carboxylic acids such as benzoic acid, p-toluic acid, and the like. As the salts of these carboxylic acids, there are exemplified sodium salts, potassium salts, magnesium salts, calcium salts, zinc salts, etc. Among them, potassium acetate and zinc acetate are preferred.

A non-nucleophilic strong base means a compound having such a strong alkalinity that it can substract a hydrogen atom bonding to the carbon atom without attacking the positively-charged carbon atom. As an illustrative example, can be given 1,5diazabicyclo[4,3,0]-nona-5-ene, 1,8-diazabicyclo[5,4,0]undeca-7-ene, 1,4-diazabicyclo[2,2,2]-octane, tetrabutyl ammonium fluoride, potassium tert-butoxide and the like.

The amount of the isomerization catalyst for the steriods having the partial general formula (II) can be chosen properly, depending upon the kind of the catalyst employed. For example, in case of a metal salt of a carboxylic acid or carbonic acid, an equimolar or more amount of the catalyst per mole of the steroid is usually employed. and 0.01 to 1 mole of the catalyst per mole of the steroid is usually employed in case of the non-nucleophilic strong base.

The reaction temperature is dependent on the isomerization catalyst and the organic polar solvent and is 20° C. to 150° C., preferably 30° C. to 100° C. The reaction is completed usually in 1 to 12 hours.

The use of a non-nucleophilic strong base as an isomerization catalyst is often preferrable in that the reaction can proceed even when a smaller amount of the catalyst is used, and the reaction product can easily be recovered by a simple means such as an extraction and the like.

After completion of the reaction, the reaction product is separated from the reaction solution by a conventional method such as solvent extraction, recrystallization, column chromatography, etc., whereby a 21-acyloxy-20-keto-delta[16]-steroid of high purity can be obtained.

The 21-acyloxy-20-keto-delta[16]-steroid thus obtained is, for example, a steroid compound represented by the structural formula:

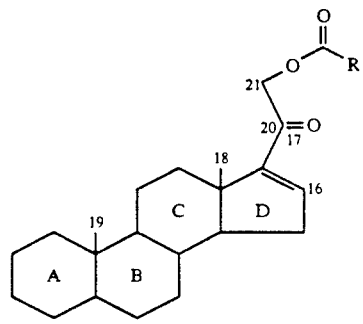

The acyloxy group at the 21-position is a group which has migrated from the 20-position of the 20-acyloxy17(20)-methylen-21-al-steroid which is an intermediate. For example, from a 20-acetoxy-17(20)-methylen-21-alsteroid, a 21-acetoxy-20-keto-delta[16]-steroid can be obtained, and from a 20-isobutyryloxy-17(20)-methylen21-al-steroid, a 21-isobutyryloxy-20-keto-delta[16]steroid can be obtained.

Also in this reaction, the substituents and structures in the portions other than the 17-, 20- and 21-positions are not changed, and steroids retaining the respective partial structures can be obtained.

These 21-acyloxy-20-keto-delta[16]-steroids are useful for synthesis of many anti-inflammatory adrenocortical steroids.

As described above, according to this invention, a 21-acyloxy-20-keto-delta16steroid can be produced by a short process economically in high yield by using as a starting material a 17α-ethynyl-17β-acyloxysteroid which can easily be produced from a 17-ketosteroid which is not expensive, converting the same into a 20-acyloxy-17(20)-methylen-21-al-steroid by oxidation reaction, and then isomerizing this compound.

The oxidation reaction of this invention is applicable not only to production of a steroid having the above partial structural formula (II) by oxidation of a steroid having the above partial structural formula (I) but also to oxidation of a compound having a structure of a formula similar to the above partial structural formula (I). That is to say, it is applicable also to production of an α-acyloxy-α,β-unsaturated carbonyl compound. This is the 2nd aspect of the invention.

α-Acyloxy-α,β-unsaturated compounds have heretofore been expected to be used as useful chemical compounds in the fields of perfumes, medicines, chemical agents, etc. and important intermediates for producing those chemicals.

There are few general methods for synthesizing such unsaturated carbonyl compounds. In the field of steroids, there is known a method for producing the unsaturated carbonyl compound which comprises preparing an α-hydroxy-α,β-unsaturated aldehyde by Mattox rearrangement [J. Am. Chem. Soc. 74, 4340 (1951)], and then acylating the aldehyde. However, this method is only for steroids and uses a complicated starting material, and hence it is not a general method.

When the oxidation reaction described above is applied to a propargyl ester represented by the general formula (V) shown below, a desired α-acyloxyα,β-unsaturated carbonyl compound (the general formula (VI) shown below) can be produced with high activity and high selectivity:

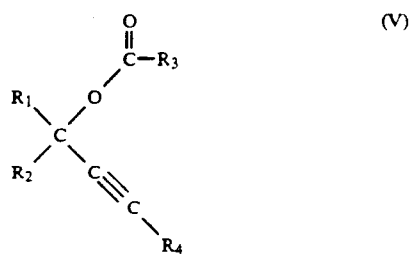

(wherein $R_1$, $R_2$ and $R_4$ are independently hydrogen atoms or substituted or unsubstituted hydrocarbon residues, or $R_1$, $R_2$ and $R_4$, when taken together with one another in an optional combination, form a ring, and $R_3$ is a substituted or unsubstituted hydrocarbon residue),

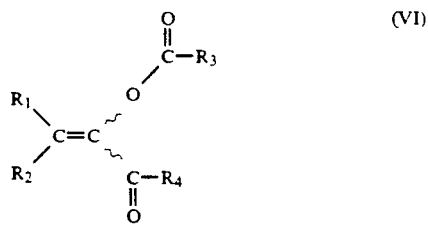

(wherein $R_1$, $R_2$, $R_3$ and $R_4$ have the same meanings as defined above, and noted that the configuration may be either E-configuration or Z-configuration).

In the above formulas, $R_1$, $R_2$ and $R_4$ are independently hydrogen atoms, or substituted or unsubstituted hydrocarbon residues. Specific examples of the hydrocarbon residues include alkyl groups such as methyl, ethyl, propyl, isopropyl, butyl, isobutyl, hexyl, octyl, decyl, and the like; alkenyl group such as allyl, pulenyl, and the like; and aryl groups such as phenyl, benzyl, and the like. These hydrocarbon residues may have substituents. As the substituents, any substituents may be selected so long as they do not affect the reaction, and there can be exemplified, for example, hydroxyl group, halide groups, amino group, carbonyl group, acyloxy groups, etc. Furthermore, the hydrocarbon residues which are optionally substituted by these substituents may be bonded to one another in an optional combination to form a ring such as cyclopentane ring, cyclohexane ring, cyclooctane ring, or the like. Although the numbers of carbon atoms of $R_1$, $R_2$ and $R_4$ are not critical, the sum of the three numbers is 100 or less, and it is preferably 50 or less from the viewpoint of the reactivity. In addition, $R_1$ and $R_2$, when taken together, may form a cyclopentanohydrophenanthlene type ring which may have an unsaturated bond in the molecule (hereinafter referred to as "cyclopentanohydrophenanthlene ring type structure") in the form of corresponding to the 1st aspect of the invention.

$R_3$ is a substituted or unsubstituted hydrocarbon residue, which includes, for example, hydrocarbon residues such as the above-mentioned alkyl groups, alkenyl groups, and aryl groups, and substituted derivatives thereof having the above-mentioned substituents. Among them, lower alkyl groups such as methyl, ethyl, propyl, isopropyl, butyl, isobutyl, pentyl, and the like are preferred from the viewpoint of ease of the reaction.

Various conditions for the reaction are the same as in the case of steroids.

EXAMPLES

This invention is more specifically illustrated with the following examples.

EXAMPLES 1

(1) Into a reactor were charged 1 m mole of 17α-ethynyl-17β-isobutyryloxy-androsta-4,9(11)-dien-3-one (A), 0.05 m mole of palladium bromide, 0.01 m mole of a 48% aqueous hydrogen bromide solution and 5 ml of ethylene glycol dimethyl ether, and stirred in the atmosphere at 60° C. for 2 hours. After completion of the reaction, the reaction mixture was cooled with water and extracted with ethyl acetate. The extract was dried over magnesium sulfate and the solvent was removed under pressure. The residue was purified by a silica gel chromatography to obtain 20-isobutyryloxy-3-oxo-pregna4,9 (11),17(20)-trien-21-al (B) in 90% yield.

(2) Subsequently, 1 m mole of the 20-isobutyryloxy3-oxo-pregna-4,9(11),17(20)-trien-21-al (B) obtained, 1.5 m moles of potassium acetate and 5 ml of dimethylformamide were charged into a reactor and stirred with heating at 60° C. for 8 hours under nitrogen. After completion of the reaction, the reaction mixture was cooled with water and extracted with ethyl acetate. The extract was dried over magnesium sulfate and the solvent was removed under reduced pressure. The residue was purified by a silica gel chromatography to obtain 21-isobutyryloxy-pregna-4,9(11),16-triene-3,20-dione (C) in 90% yield.

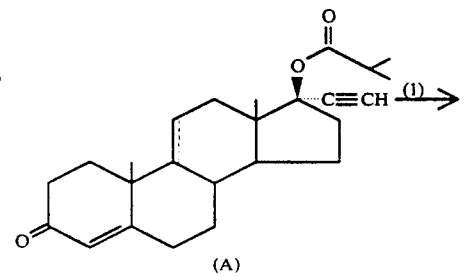

-continued

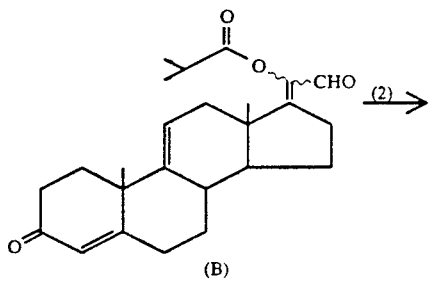

(B)

-continued

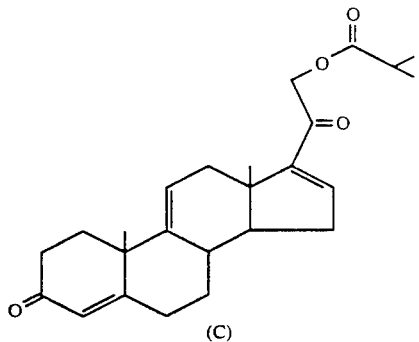

(C)

EXAMPLE 2

(1) In the same manner as in Example 1(1), except that each steroid compound listed in Table 1 was reacted as a starting material for the predetermined time shown in Table 1, reaction intermediates were obtained in the yields shown in Table 1.

(2) Subsequently, in the same manner as in Example 1(2), except that each of the reaction intermediates thus obtained was reacted for the predetermined time shown in Table 1, desired compounds were obtained in the yields shown in Table 1.

TABLE 1

| No. of run | Starting material | Reaction time (hr) | Starting material | Yield (%) | Reaction time (hr) | Desired compound | Yield (%) |
|---|---|---|---|---|---|---|---|
| 2-1* | steroid with OAc and C≡CH | 2 | steroid with AcO and CHO | 70 | 6 | steroid with OAc and C=O | 94 |
| 2-2 | steroid with isobutyryloxy and C≡CH | 2 | steroid with isobutyryloxy and CHO | 90 | 9 | steroid with isobutyryloxy-CH₂-C=O | 90 |
| 2-3 | steroid with isobutyryloxy and C≡CH | 2 | steroid with isobutyryloxy and CHO | 80 | 7 | steroid with isobutyryloxy-CH₂-C=O | 80 |

TABLE 1-continued

| No. of run | Starting material | Reaction time (hr) | Starting material | Yield (%) | Reaction time (hr) | Desired compound | Yield (%) |
|---|---|---|---|---|---|---|---|
| 2-4 | (structure with C≡CH, HO, isobutyrate) | 3 | (structure with CHO, HO, isobutyrate) | 65 | 10 | (structure with HO, enone, isobutyrate ester) | 80 |
| 2-5 | (structure with C≡CH, C=O, isobutyrate) | 2 | (structure with CHO, C=O, isobutyrate) | 70 | 9 | (structure with C=O, enone, isobutyrate ester) | 85 |

*Ac is an acetyl group.

EXAMPLE 3

Into a reactor were charged 1 m mole of 17α-ethynyl-17β-isobutryloxy-androsta-4,9(11)-dien-3-one, 0.05 m mole of palladium bromide, 0.01 m mole of a 48% aqueous hydrogen bromide solution and 5 ml of dimethylformamide, and stirred in the atmosphere at 60° C. for 2 hours. After completion of the oxidation reaction, no isolation procedure was carried out. The air in the reactor was replaced with nitrogen, after which 1.5 m moles of potassium acetate was added and the resulting mixture was stirred with heating at 60° C. for 9 hours. After completion of the reaction, the reaction mixture was cooled with water and extracted with ethyl acetate. The extract was dried over magnesium sulfate and the solvent was removed under reduced pressure. The residue was purified by a silica gel chromatography to obtain 21-isobutyryloxy-pregna-4,9(11),16-triene-3,20-dione in 83% yield.

EXAMPLE 4

In the same manner as in Example 1, except that zinc acetate was used in place of potassium acetate in Example 1(2), 21-isobutyryloxy-pregna-4,9(11),16-triene-3,20-dione was obtained in 80% yield.

EXAMPLE 5

In the same manner as in Example 1(1), except that each catalyst listed in Table 2 was used in place of palladium bromide and that the reaction was carried out for the predetermined time shown in Table 2, 20-isobutyryloxy-3-oxo-pregna-4,9(11),17(20)-trien-21-al was obtained in the yield shown in Table 2.

TABLE 2

| No. of run | Catalyst | Reaction time (hr) | Yield (%) |
|---|---|---|---|
| 5-1 | Palladium chloride | 12 | 40 |
| 5-2 | Sodium palladium (II) chloride | 10 | 60 |
| 5-3 | Dichlorobis(acetonitrile)palladium | 12 | 60 |
| 5-4 | Dichlorobis(benzonitrile)palladium | 12 | 70 |

EXAMPLE 6

In the same manner as in Example 1(1), except that 10 m moles of formic acid was used in place of the 48% aqueous hydrogen bromide solution, that 0.05 m mole of each copper compound listed in Table 3 was added as a co-catalyst, and that the reaction was carried out for the predetermined time shown in Table 3, 20-isobutyryloxy-3-oxo-pregna-4,9(11),17(20)-trien-21-al was obtained in the yield shown in Table 3.

TABLE 3

| No. of run | Co-catalyst | Reaction time (hr) | Yield (%) |
|---|---|---|---|
| 6-1 | Cupric acetate | 7 | 73 |
| 6-2 | Cupric bromide | 5 | 80 |
| 6-3 | Cupric formate | 7 | 70 |

EXAMPLE 7

In the same manner as in Example 1(1), except that 10 m moles of each acid listed in Table 4 was used in place of the 48% aqueous hydrogen bromide solution and that the reaction was carried out for the predetermined time shown in Table 4, 20-isobutyryoxy-3-oxopregna-4,9(11,),17(20)-trien-21-al was obtained in the yield shown in Table 4.

TABLE 4

| No. of run | Acid | Reaction time (hr) | Yield (%) |
|---|---|---|---|
| 7-1 | Formic acid | 10 | 70 |
| 7-2 | p-Toluenesulfonic acid | 15 | 30 |

EXAMPLE 8

In the same manner as in Example 1(1), except that each solvent listed in Table 5 was used in place of ethylene glycol dimethyl ether and that the reaction was carried out for the predetermined time shown in Table 5, 20-isobutyryloxy-3-oxo-pregna-4,9(11),17(20)-trien-21-al was obtained in the yield shown in Table 5.

TABLE 5

| No. of run | Solvent | Reaction time (hr) | Yield (%) |
|---|---|---|---|
| 8-1 | Dimethylformamide | 4 | 70 |
| 8-2 | Acetonitrile | 4 | 60 |
| 8-3 | Diethylene glycol dimethyl ether | 2 | 75 |
| 8-4 | Dimethyl sulfoxide | 7 | 50 |

Into a reactor were charged 1 m mole of each starting compound listed in Table 6, 0.05 m mole of palladium bromide, 0.01 m mole of a 48% aqueous hydrogen bromide solution and 5 ml of ethylene glycol dimethyl ether, and stirred in the atmosphere at 60° C. for 2 hours. After completion of the reaction, the reaction mixture was cooled with water and extracted with ethyl acetate. The extract was dried over magnesium sulfate and the solvent was removed under reduced pressure. The residue was purified by a silica gel chromatography to obtain a reaction product listed in Table 6.

The yields and physical properties of the products thus obtained are tabulated in Table 6.

TABLE 6

| No. of run | Starting compound | Reaction product | Yield (%) | Production ratio E-form/Z-form | NMR spectrum (CDCl₃), δ ppm E-form | NMR spectrum (CDCl₃), δ ppm Z-form | Mass spectrum M/e; M⁺ |
|---|---|---|---|---|---|---|---|
| 9-1 | 17α-Ethynyl-17β-isobutyryloxy-androsta-4,9(11)-dien-3-one | 20-Isobutyryloxy-3-oxo-pregna-4,9(11),17(20)-trien-21-al | 90 | 1/15 | 0.94(s, 3H) 1.36(s, 3H) 5.55(s, 1H) 5.77(s, 1H) 9.77(s, 1H) | 0.94(s, 3H) 1.35(s, 3H) 5.51(s, 1H) 5.77(s, 1H) 9.60(s, 1H) | 396 |
| 9-2 | 17α-Ethynyl-17β-acetoxy-androsta-4,9(11)-dien-3-one | 20-Acetoxy-3-oxo-pregna-4,9(11),17(20)-trien-21-al | 70 | 1/15 | 0.94(s, 3H) 1.37(s, 3H) 2.23(s, 3H) 5.56(s, 1H) 5.77(s, 1H) 9.77(s, 1H) | 0.94(s, 3H) 1.35(s, 3H) 2.26(s, 3H) 5.53(s, 1H) 5.77(s, 1H) 9.62(s, 1H) | 368 |

TABLE 6-continued
| No. of run | Starting compound | Reaction product | Yield (%) | Production ratio E-form/ Z-form | NMR spectrum (CDCl$_3$), δ ppm | | Mass spectrum M/e; M+ |
|---|---|---|---|---|---|---|---|
| | | | | | E-form | Z-form | |
| 9-3 |  17α-Ethynyl-17β-acetoxy-androsta-4-en-3-one | 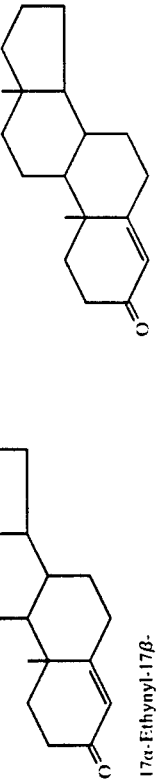 20-Acetoxy-3-oxo-pregna-4,17(20)-dien-21-al | 70 | 1/15 | 1.00(s, 3H) 1.21(s, 3H) 2.21(s, 3H) 5.75(s, 1H) 9.80(s, 1H) | 1.00(s, 3H) 1.20(s, 3H) 2.24(s, 3H) 5.75(s, 1H) 9.58(s, 1H) | 370 |

EXAMPLE 10

Into a reactor were charged 0.6 m mole of 17α-ethynyl-17β-propionyloxy-androsta-4,9(11)-dien-3-one, 0.06 m mole of sodium palladium (II) chloride, 1 ml of formic acid and 5 ml of dimethylformamide, and stirred in the atmosphere at 60° C. for 7 hours. After completion of the reaction, the reaction mixture was treated in the same manner as in Example 9 to obtain 20-propionyloxy-3-oxo-pregna-4,9(11),17(20)-trien-21-al in 38.4% yield.

Physical properties of the product are tabulated in Table 7.

EXAMPLE 11

Into a reactor were charged 0.3 m mole of 17α-ethynyl-17β-butyryloxy-androsta-4,9(11)-dien-3-one, 0.03 m mole of sodium palladium (II) chloride, 0.2 ml of formic acid and 3 ml of ethylene glycol dimethyl ether, and stirred in the atmosphere at 60° C. for 15 hours. After completion of the reaction, the reaction mixture was treated in the same manner as in Example 9 to obtain 20-butyryloxy-3-oxo-pregna-4,9(11),17(20)-trien-21-al in 47.7% yield.

Physical properties of the product are tabulated in Table 8.

TABLE 8

| Starting compound | Reaction product | Production ratio E-form/Z-form | NMR spectrum (CDCl$_3$), δppm E-form | NMR spectrum (CDCl$_3$), δppm Z-form | Mass spectrum M/e; M$^+$ |
|---|---|---|---|---|---|
| 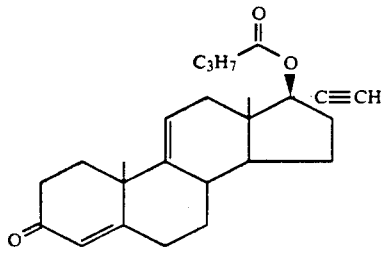<br>17α-Ethynyl-17β-butyryloxy-androsta-4,9(11)-dien-3-one | 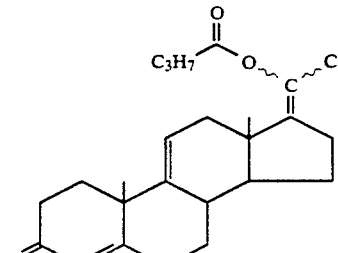<br>20-Butyryloxy-3-oxo-pregna-4,9(11),17(20)-trien-21-al | 1/45 | 0.94(s,3H)<br>1.05(t,3H)<br>1.37(s,3H)<br>5.52(s,1H)<br>5.76(s,1H)<br>9.76(s,1H) | 0.93(s,3H)<br>1.04(t,3H)<br>1.35(s,3H)<br>5.52(s,1H)<br>5.76(s,1H)<br>9.60(s,1H) | 396 |

EXAMPLE 12

Into a reactor were charged 0.37 m mole of 17α-ethynyl-17β-isovaleryloxy-androsta-4,9(11)-dien3-one, 0.04 m mole of sodium palladium (II) chloride, 0.25 ml of formic acid and 3.5 ml of ethylene glycol dimethyl ether, and stirred in the atmosphere at 60° C. for 15 hours. After completion of the reaction, the reaction mixture was treated in the same manner as in Example 9 to obtain 20-isovaleryloxy-3-oxo-pregna4,9(11),17(20)-trien-21-al in 51.1% yield.

Physical properties of the product are tabulated in Table 9.

TABLE 7

| Starting compound | Reaction product | Production ratio E-form/Z-form | NMR spectrum (CDCl$_3$), δppm E-form | NMR spectrum (CDCl$_3$), δppm Z-form | Mass spectrum M/e; M$^+$ |
|---|---|---|---|---|---|
| 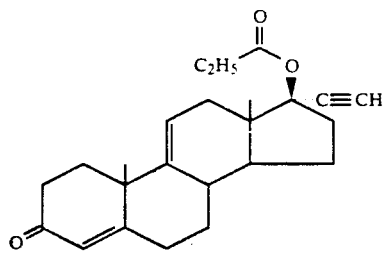<br>17α-Ethynyl-17β-propionyloxy-androsta-4,9(11)-dien-3-one | 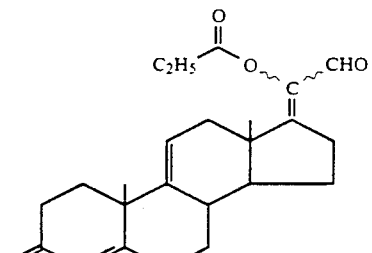<br>20-Propionyloxy-3-oxo-pregna-4,9(11),17(20)-trien-21-al | 1/13 | 0.94(s,3H)<br>1.25(t,3H)<br>1.35(s,3H)<br>5.55(s,1H)<br>5.75(s,1H)<br>9.80(s,1H) | 0.94(s,3H)<br>1.23(t,3H)<br>1.33(s,3H)<br>5.55(s,1H)<br>5.75(s,1H)<br>9.52(s,1H) | 382 |

TABLE 9

| Starting compound | Reaction product | Production ratio E-form/Z-form | NMR spectrum (CDCl₃), δppm E-form | NMR spectrum (CDCl₃), δppm Z-form | Mass spectrum M/e; M⁺ |
|---|---|---|---|---|---|
| 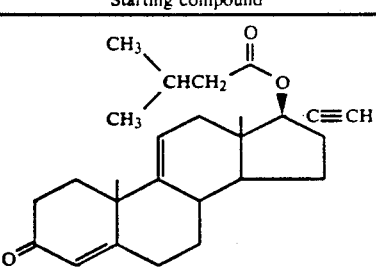 17α-Ethynyl-17β-iso-valeryloxy-androsta-4,9(11)-dien-3-one | 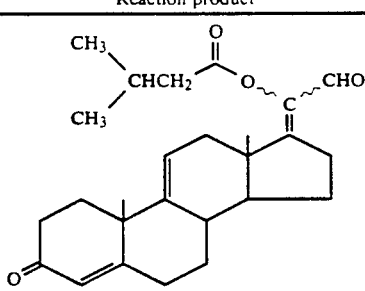 20-Isovaleryloxy-3-oxo-pregna-4,9(11),17(20)-trien-21-al | 1/4 | 0.94(s,3H) 1.05(d,6H) 1.37(s,3H) 5.51(s,1H) 5.75(s,1H) 9.77(s,1H) | 0.93(s,3H) 1.04(d,6H) 1.35(s,3H) 5.51(s,1H) 5.75(s,1H) 9.59(s,1H) | 410 |

REFERENTIAL EXAMPLE 1

Into a reactor were charged 1 m mole of the reaction product (a mixture of E-form and Z-form) obtained in Run No. 9-3 of Example 9, 1.5 m moles of potassium acetate and 5 ml of dimethylformamide, and stirred with heating at 50° C. for 8 hours under nitrogen. After completion of the reaction, the reaction mixture was cooled with water and extracted with ethyl acetate. The extract was dried over magnesium sulfate and the solvent was removed under reduced pressure. The residue was purified by a silica gel chromatography to obtain 21-acetoxypregna-4,16-diene-3,20-dione of the following formula in 85% yield:

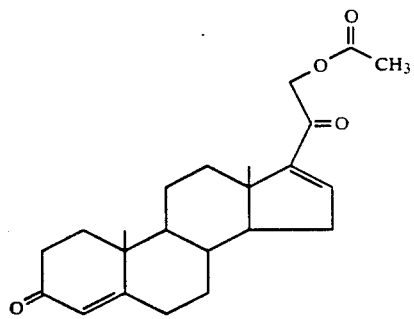

REFERENTIAL EXAMPLE 2

Into a reactor were charged 0.2 m mole of the 20-propionyloxy-3-oxo-pregna-4,9(11),17(20)-trien-21-al obtained in Example 10, 0.3 m mole of potassium acetate and 2 ml of dimethylformamide, and stirred under nitrogen at room temperature for 2 days. Then, the resulting mixture was heated to 50% and stirred for 10 hours. After completion of the reaction, the reaction mixture was treated in the same manner as in Referential Example 1 to obtain 21-propionyloxy-pregna-4,9(11),16-triene-3,20-dione of the following structural formula in 78.2% yield:

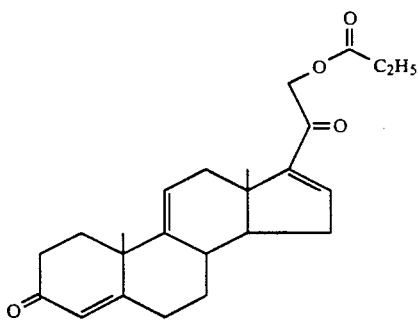

REFERENTIAL EXAMPLE 3

Into a reactor were charged 0.14 m mole of the 20-butyryloxy-3-oxo-pregna-4,9(11),17(20)-trien21-al obtained in Example 11, 0.3 m mole of potassium acetate and 2 ml of dimethylformamide, and stirred under nitrogen at 55° C. for 9 hours. After completion of the reaction, the reaction mixture was treated in the same manner as in Referential Example 1 to obtain 21-butyryloxy-pregna-4,9(11),16-triene-3,20-dione of the following structural formula in 82.4% yield:

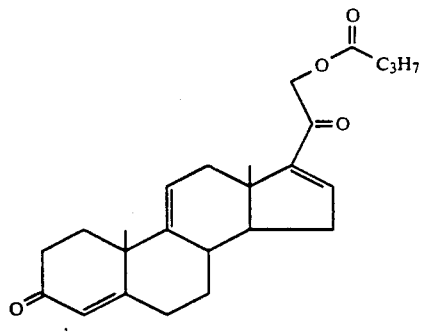

REFERENTIAL EXAMPLE 4

Into a reactor were charged 0.19 m mole of the 20-isovaleryloxy-3-oxo-pregna-4,9(11),17(20)-trien-21-al obtained in Example 12, 0.29 m mole of potassium acetate and 2 ml of dimethylformamide, and stirred under nitrogen at 55° C. for 9 hours. After completion of the reaction, the reaction mixture was treated in the same manner as in Referential Example 1 to obtain 21-isovaleryloxy-pregna-4,9(11),16-trien-3,20-dione of the following structural formula in 85.8% yield:

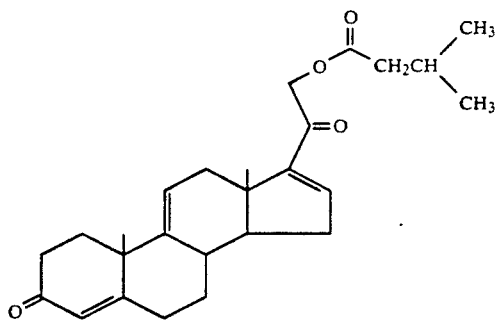

REFERENTIAL EXAMPLE 5

Into a reactor were charged 0.26 m mole of the 20-isobutyryloxy-3-oxo-pregna-4,9(11),17(20)-trien-21-al, 2 ml of dimethylformamide and a given amount of the isomerization catalyst listed in Table 9(a). The reaction was carried out under conditions shown in Table 9(a) under stream of nitrogen gas. After the completion of the reaction, the reaction mixture was treated in the same manner as in Referential Example 1 to obtain 21-isobutyryloxy-pregna-4,9(11),16-trien3,20-dione in the yields shown in Table 9(a), respectively.

peroxide solution was added with stirring so that the resulting mixture contained 9 m moles of hydrogen peroxide. Subsequently, 5 ml of ethylene glycol dimethyl ether was added, after which 5 ml of a solution of 3 m moles of 17α-ethynyl-17β-isobutyryloxyandrosta-4,9(11)-dien-3-one in ethylene glycol dimethyl ether was added dropwise in a nitrogen stream at 60° C. over a period of 10 minutes. Then, the reaction was carried out for 4 hours. After completion of the reaction, the reaction mixture was cooled with water and extracted with ethyl acetate. The extract was dried over magnesium sulfate and the solvent was removed under reduced pressure. The residue was purified by a silica gel chromatography to obtain 20-isobutyryloxy-3-oxopregna-4,9(11),17(20)-trien-21-al in 74% yield.

EXAMPLE 14

Into a reactor were charged 1 m mole of each starting compound (compounds 1 to 5) listed in Table 10, 0.05 m mole of palladium bromide, 0.01 m mole of a 48% aqueous hydrogen bromide solution and 5 ml of ethylene glycol dimethyl ether, and stirred in the atmosphere at 60° C. for 2 hours. After completion of the reaction, the reaction mixture was cooled with water and extracted with ethyl acetate. The extract was dried over magnesium sulfate and the solvent was removed under reduced pressure. The residue was purified by a silica gel chromatography. Thus, the reaction products (compounds 7 to 11) were obtained in the respective yields shown in Table 10.

TABLE 9(a)

| No. of run | Isomerization catalyst | | Reaction conditions | | Yield (%) |
|---|---|---|---|---|---|
| | Catalyst used | Amount *1 (in molar ratio) | Temp. (°C.) | Hours | |
| Ref. Run 5-1 | Tetrabutyl ammonium fluoride | 1.0 | 50 | 1 | 85 |
| Ref. Run 5-2 *2 | 1,4-diazabicyclo[2,2,2]-octane | 1.0 | 50 70 | 4 10 | 65 |
| Ref. Run 5-3 | 1,8-diazabicyclo[5,4,0]-undeca-7-ene | 1.0 | 50 | 1.5 | 76 |
| Ref. Run 5-4 | 1,8-diazabicyclo[5,4,0]-undeca-7-ene | 0.5 | 50 | 3.5 | 75 |
| Ref. Run 5-5 | 1,8-diazabicyclo[5,4,0]-undeca-7-ene | 0.25 | 50 | 12 | 81 |
| Ref. Run 5-6 | 1,5-diazabicyclo[4,3,0]-nona-5-ene | 0.5 | 50 | 7 | 80 |

*1: shown in terms of the mole of the catalyst used per mole of the steriod used
*2: After having been subjected to reaction at 50° C. for 4 hrs., the reaction was continued for another 10 hrs at 70° C.

EXAMPLE 13

In a reactor was placed 0.12 m mole of potassium palladium (II) bromide, and a 35% aqueous hydrogen The reaction products were identified by NMR analysis and mass spectrometry.

TABLE 10

| No. of run | Starting compound | | Reaction product* | | Yield (%) |
|---|---|---|---|---|---|
| 14-1 | [structure with O-C(=O)-CH(CH₃)₂ and C≡CH on cyclohexane] | Compound 1 | [structure with O-C(=O)-CH(CH₃)₂ and =C-CHO on cyclohexane] | Compound 7 | 80 |

TABLE 10-continued

| No. of run | Starting compound | Reaction product* | Yield (%) |
|---|---|---|---|
| 14-2 | 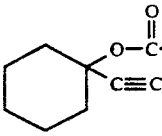 Compound 2 | 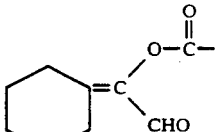 Compound 8 | 60 |
| 14-3 | 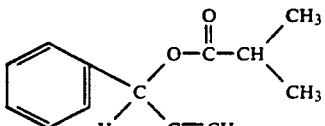 Compound 3 | 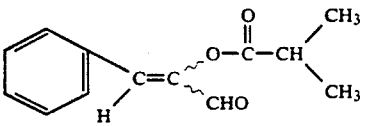 Compound 9 | 50 |
| 14-4 | 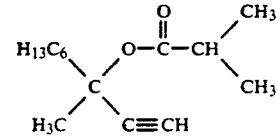 Compound 4 | 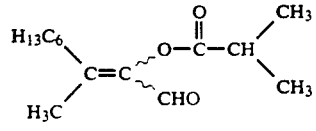 Compound 10 | 70 |
| 14-5 | 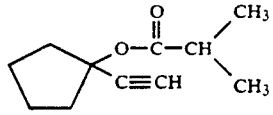 Compound 5 | 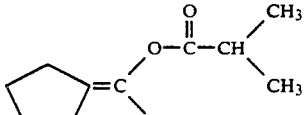 Compound 11 | 50 |

*In the structural formulas, ∼ indicates that the configuration is E-configuration or Z-configuration.

EXAMPLE 15

Compound 7 was obtained in the same manner as in Run No. 14-1 of Example 14, except that each catalyst listed in Table 11 was used in place of palladium bromide and the predetermined reaction time shown in Table 11 was employed. The yields are tabulated in Table 11.

TABLE 11

| No. of run | Catalyst | Reaction time (hr) | Yield (%) |
|---|---|---|---|
| 15-1 | Palladium chloride | 12 | 40 |
| 15-2 | Sodium palladium (II) chloride | 15 | 60 |
| 15-3 | Dichlorobis(acetonitrile)palladium | 12 | 60 |
| 15-4 | Dichlorobis(benzonitrile)palladium | 12 | 70 |

EXAMPLE 16

Compound 7 was obtained in 30% in the same manner as in Run No. 14-1 of Example 14, except that m moles of p-toluenesulfonic acid was used in place of the 48% aqueous hydrogen bromide solution and that the reaction time was 15 hours.

EXAMPLE 17

Compound 7 was obtained in the same manner as in Run No. 14-1 of Example 14, except that 10 m moles of formic acid was used in place of the 48% aqueous hydrogen bromide solution, that no co-catalyst or 0.05 m mole of each co-catalyst listed in Table 12 was added, and that the reaction was carried out for the predetermined time shown in Table 12. The yields are tabulated in Table 12.

TABLE 12

| No. of run | Co-catalyst | Reaction time (hr) | Yield (%) |
|---|---|---|---|
| 17-1 | — | 10 | 70 |
| 17-2 | Cupric acetate | 7 | 73 |
| 17-3 | Cupric bromide | 5 | 80 |
| 17-4 | Cupric formate | 7 | 70 |

EXAMPLE 18

Compound 7 was obtained in 20% yield in the same manner as in Run No. 14-1 of Example 14, except that dimethylformamide was used in place of ethylene glycol dimethyl ether, that no 48% aqueous bromide solution was added, and that the reaction time was 24 hours.

EXAMPLE 19

Compound 7 was obtained in the same manner as in Run No. 14-1 of Example 14, except that each solvent listed in Table 13 was used in place of ethylene glycol dimethyl ether and that the predetermined reaction time shown in Table 13 was employed. The yields are tabulated in Table 13.

TABLE 13

| No. of run | Solvent | Reaction time (hr) | Yield (%) |
|---|---|---|---|
| 19-1 | Dimethylformamide | 4 | 70 |
| 19-2 | Acetonitrile | 4 | 70 |
| 19-3 | Diethylene glycol dimethyl ether | 2 | 75 |
| 19-4 | Dimethyl sulfoxide | 7 | 60 |

What is claimed is:

1. A process for producing an $\alpha$-acyloxy-$\alpha,\beta$-unsaturated carbonyl compound represented by the general formula (VI):

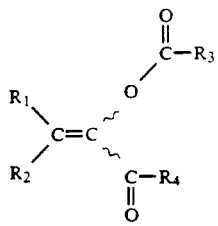 (VI)

wherein $R_1$, $R_2$ and $R_4$ are independently hydrogen atoms or substituted or unsubstituted alkyl, alkenyl, aryl or aralkyl groups, or $R_1$ and $R_2$, when taken together with one another form a ring, $R_3$ is a substituted or unsubstituted alkyl, alkenyl, aryl or aralkyl group, and ⁓ indicates that the configuration may be either E-configuration or Z-configuration, which comprises bringing a propargyl ester represented by the general formula (V):

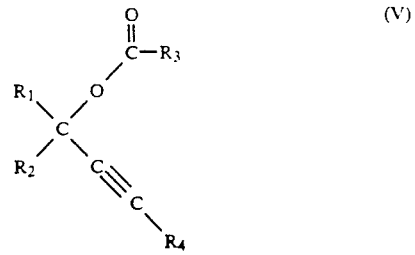 (V)

wherein $R_1$, $R_2$, $R_3$ and $R_4$ have the same meanings as defined above, into contact with a platinum group metal compound catalyst in the presence of oxygen and/or a peroxide.

2. A process according to claim 1, wherein the platinum group metal compound catalyst is a palladium compound.

3. A process according to claim 1, wherein a copper compound is used as a co-catalyst with the platinum group metal compound catalyst.

4. A process according to claim 1, wherein the propargyl ester and the catalyst are contacted in the presence of an acid and oxygen and/or a peroxide.

5. A process according to claim 1, wherein the sum of the numbers of carbon atoms of $R_1$, $R_2$ and $R_4$ is 100 or less.

6. A process according to claim 5, wherein $R_3$ is a lower alkyl group.

* * * * *